(12) United States Patent
Nishida et al.

(10) Patent No.: US 10,386,122 B2
(45) Date of Patent: Aug. 20, 2019

(54) NUCLEATION DEVICE, HEAT STORAGE DEVICE, AND NUCLEATION METHOD FOR HEAT STORAGE MATERIAL

(71) Applicant: KITAGAWA INDUSTRIES CO., LTD., Aichi (JP)

(72) Inventors: Shinji Nishida, Kasugai (JP); Hiroto Yoshino, Kasugai (JP); Teruaki Yuoka, Kasugai (JP)

(73) Assignee: KITAGAWA INDUSTRIES CO., LTD., Aichi (JP)

( * ) Notice: Subject to any disclaimer, the term of this patent is extended or adjusted under 35 U.S.C. 154(b) by 456 days.

(21) Appl. No.: 15/336,994

(22) Filed: Oct. 28, 2016

(65) Prior Publication Data

US 2017/0122674 A1    May 4, 2017

(30) Foreign Application Priority Data

Oct. 30, 2015 (JP) .................... 2015-213878

(51) Int. Cl.
*F28D 20/02* (2006.01)
*B01D 9/00* (2006.01)
*A61F 7/02* (2006.01)
*C30B 7/00* (2006.01)

(52) U.S. Cl.
CPC .......... *F28D 20/028* (2013.01); *B01D 9/005* (2013.01); *F28D 20/02* (2013.01); *A61F 2007/0293* (2013.01); *C30B 7/00* (2013.01); *Y02E 60/145* (2013.01)

(58) Field of Classification Search
CPC ............. F28D 20/028; F28D 20/02; A61F 2007/0293; B01D 9/005; C30B 7/00; Y02E 60/145
See application file for complete search history.

(56) References Cited

U.S. PATENT DOCUMENTS

| | | | | |
|---|---|---|---|---|
| 2,289,425 A * | 7/1942 | Hogan | ........... | A47J 36/28 126/263.03 |
| 4,372,127 A * | 2/1983 | Pohlmann | ........... | F28D 19/04 62/6 |
| 4,532,110 A * | 7/1985 | Kapralis | ........... | B01D 9/0013 422/245.1 |
| 4,899,727 A * | 2/1990 | Kapralis | ........... | F28D 20/028 126/263.04 |
| 5,056,589 A * | 10/1991 | Hettel | ........... | F28D 20/028 126/263.04 |
| 5,378,337 A * | 1/1995 | Kiyomura | ........... | F28D 20/028 204/230.3 |
| 7,318,885 B2 * | 1/2008 | Omasa | ........... | C25B 1/04 204/261 |
| 7,459,071 B2 * | 12/2008 | Omasa | ........... | C25B 1/04 204/242 |

(Continued)

FOREIGN PATENT DOCUMENTS

JP      60-251189      12/1985

*Primary Examiner* — Jon T. Schermerhorn, Jr.
(74) *Attorney, Agent, or Firm* — Wenderoth, Lind & Ponack, L.L.P.

(57) ABSTRACT

A nucleation device for changing a phase of a heat storage material from a liquid state to a solid state includes a plurality of substrates in close contact with each other in the heat storage material, and a pressing part that presses a portion of the plurality of substrates so as to elicit a change in the state of close contact of the plurality of substrates.

3 Claims, 11 Drawing Sheets

(56) References Cited

U.S. PATENT DOCUMENTS

| | | | |
|---|---|---|---|
| 7,708,009 B1* | 5/2010 | Collins | A61F 7/03 |
| | | | 126/204 |
| 7,730,863 B2* | 6/2010 | Shikida | F28D 20/028 |
| | | | 123/142.5 R |
| 2002/0043260 A1* | 4/2002 | Layer | A61F 7/0085 |
| | | | 126/263.01 |
| 2004/0065314 A1* | 4/2004 | Layer | A61F 7/0085 |
| | | | 126/263.03 |
| 2014/0131012 A1* | 5/2014 | Yagi | F28D 20/028 |
| | | | 165/104.21 |

* cited by examiner

NUCLEATION DEVICE, HEAT STORAGE DEVICE, AND NUCLEATION METHOD FOR HEAT STORAGE MATERIAL

CROSS REFERENCE TO RELATED APPLICATION

This application claims priority from Japanese Patent Application No. 2015-213878 filed on Oct. 30, 2015. The entire contents of the priority application are incorporated herein by reference

TECHNICAL FIELD

The technology disclosed in the present specification relates to a nucleation device and a heat storage device.

BACKGROUND ART

Examples of technologies known in the art include Japanese Unexamined Patent Application Publication No. S60-251189A (hereinafter, referred to as "Patent Literature 1"), in which a heat storage device is recited that uses solidification heat, released when heat storage material phase changes from a liquid to a solid, as a heat source. This heat storage device includes heat storage material that releases heat when phase changing from a liquid state to a solid state, a metal strip that serves as a trigger for nucleation that promotes the phase change of the heat storage material, and a container that houses the heat storage material and the strip. When using the heat storage material as a heat source, the heat storage material is impacted by pinching the container from the outside by fingers and snap displacing the strip. Upon the snap displacing, the heat storage material is nucleated and the heat storage material phase changes from a liquid to a solid, thereby releasing the solidification heat of the heat storage material.

CITATION LIST

Patent Literature

Patent Literature 1: Japanese Unexamined Patent Application Publication No. S60-251189A

SUMMARY OF INVENTION

Technical Problem

In the engines and the like of vehicles, there is a tendency for resistance due to slide friction to increase while warming-up is incomplete. As such, research is being conducted regarding the application of heat storage devices to engines and the like.

However, if the heat storage device described above is installed around the engine of a vehicle, it will not be possible to press/operate the container from the outside and cause the nucleation of the heat storage material. Additionally, with the heat storage device described above, there is a problem of low nucleation reliability due to repeated use.

In the present specification, technology for improving the nucleation reliability of a heat storage material installed at a remote location is disclosed.

Solution to Problem

The technology disclosed in the present specification is a nucleation device for changing the phase of a heat storage material from a liquid state to a solid state. Such a device has a configuration including a plurality of substrates in close contact with each other in the heat storage material; and a pressing part that presses a portion of the plurality of substrates so as to elicit a change in the state of close contact of the plurality of substrates.

Additionally, the art disclosed in the present specification is a heat storage device. Such a device has a configuration including a heat storage material that phase changes from a liquid state to a solid state; the nucleation device described above; and a container that houses the heat storage material and the nucleation device.

Additionally, the technology disclosed in the present specification is a nucleation method for a heat storage material. The method includes the steps of disposing a plurality of substrates in close contact with each other in a heat storage material; and pressing a portion of the plurality of substrates so as to elicit a change in the state of close contact of the plurality of substrates, thereby causing the heat storage material to nucleate.

According to the nucleation device with the configuration described above, the state of close contact of the plurality of substrates is changed by the pressing by the pressing member and the heat storage material, which is in the state of close contact, nucleating due to this change. Accordingly, the change in the state of close contact of the plurality of substrates can be elicited and the heat storage material can be caused to nucleate by operating the pressing part through remote operation or the like at a location separated from the heat storage material. That is, nucleation reliability of the heat storage material installed at a remote location can be improved and solidification heat of the heat storage material can be reliably released.

The nucleation device disclosed in the present specification may be configured as follows.

The pressing part may be configured to directly press the substrates.

With such a configuration, the change in the state of close contact of the substrates can be elicited and the heat storage material can be caused to nucleate with less pressing force compared to indirectly pressing the substrates.

The pressing part may be configured to press so as to impact the substrates.

With such a configuration, the pressing is performed so as to strike or otherwise impact the substrates. Thereby, the change in the state of close contact of the substrates can be elicited with less pressing force compared to a case where pressing is performed so as not to impact the substrates.

A configuration is possible in which a portion among the plurality of substrates is a fastened portion that includes a male screw portion; and another portion among the plurality of substrates is a fastening portion that includes a female screw portion that screws onto the male screw portion.

With such a configuration, the state of close contact can be formed using a simple configuration such as one in which the female screw portion of the fastening portion is screwed onto the male screw portion of the fastened portion.

A configuration is possible in which a portion among the plurality of substrates is a flat plate member, and the plate member is sandwiched by the fastened portion and the fastening portion so as to be in close contact with the fastened portion and the fastening portion.

With such a configuration, locations, where the state of close contact exists due to the plate member being sandwiched by the fastened portion and the fastening portion, are formed at a plurality of sites between the plate member and the fastened portion and between the plate member and the fastening portion. As such, the nucleation reliability can be improved.

A configuration is possible in which the heat storage material is sodium acetate trihydrate.

With such a configuration, the heat storage device can be configured without preparing a seed material for the nucleation of sodium acetate anhydrate or the like that causes the solidification of the sodium acetate trihydrate.

Advantageous Effects of Invention

According to the technology disclosed in the present specification, the nucleation reliability of a heat storage material installed at a remote location can be improved.

DESCRIPTION OF EMBODIMENTS

First Embodiment

A first embodiment according to the technology disclosed in the present specification is described while referencing FIGS. 1 to 8.

The present embodiment illustrates an example of a heat storage device 10 that uses solidification heat, released when heat storage material 11 phase changes from a liquid to a solid, as a heat source. Note that in the following description, an "up-down direction" is based on an up-down direction in FIGS. 1 and 5, and a "left-right direction" is based on a left-right direction in FIGS. 1 and 5.

Figure 1:
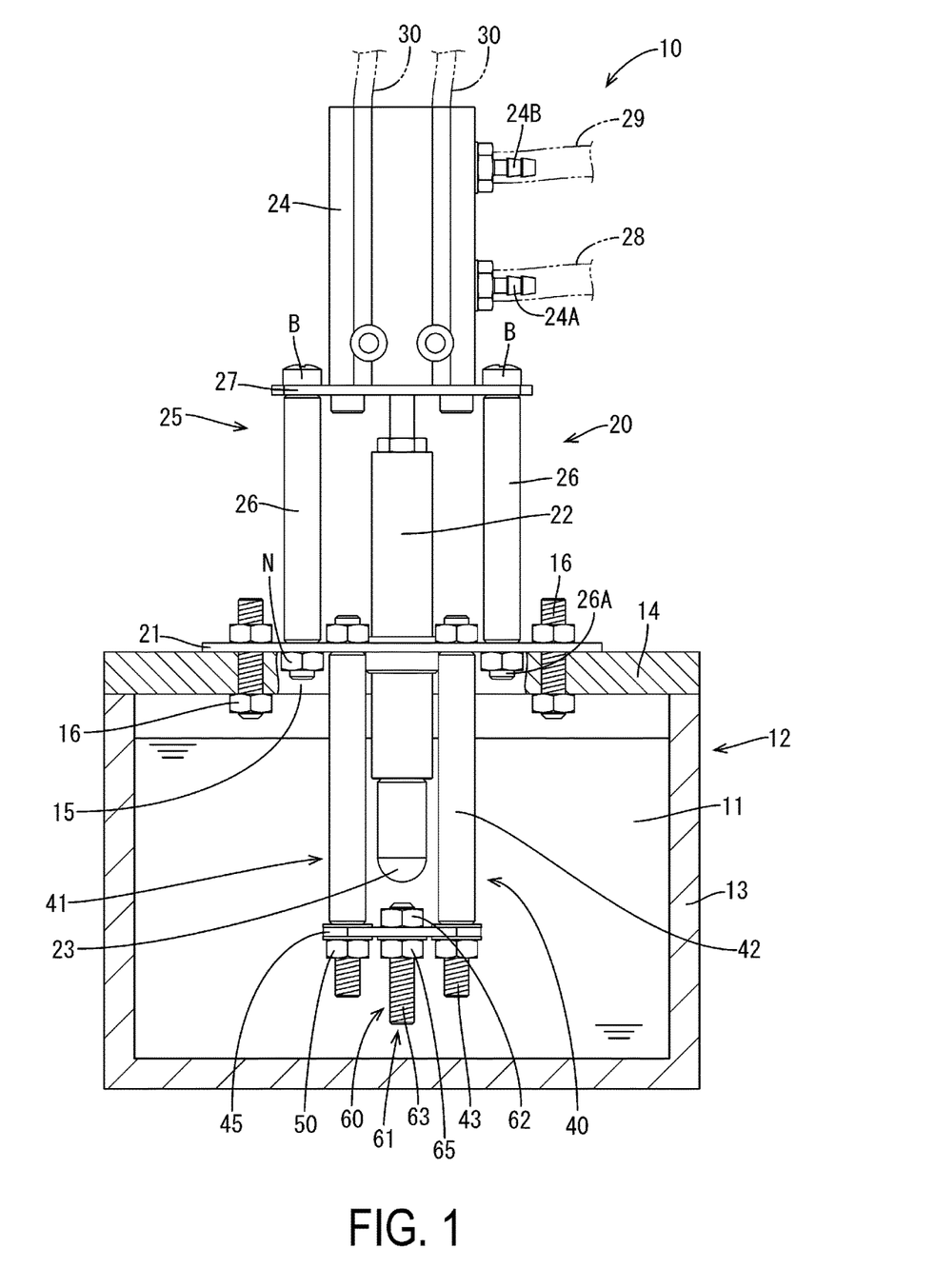
FIG. 1 is a partial cutaway cross-sectional view of a heat storage device according to a first embodiment.
Figure 2:
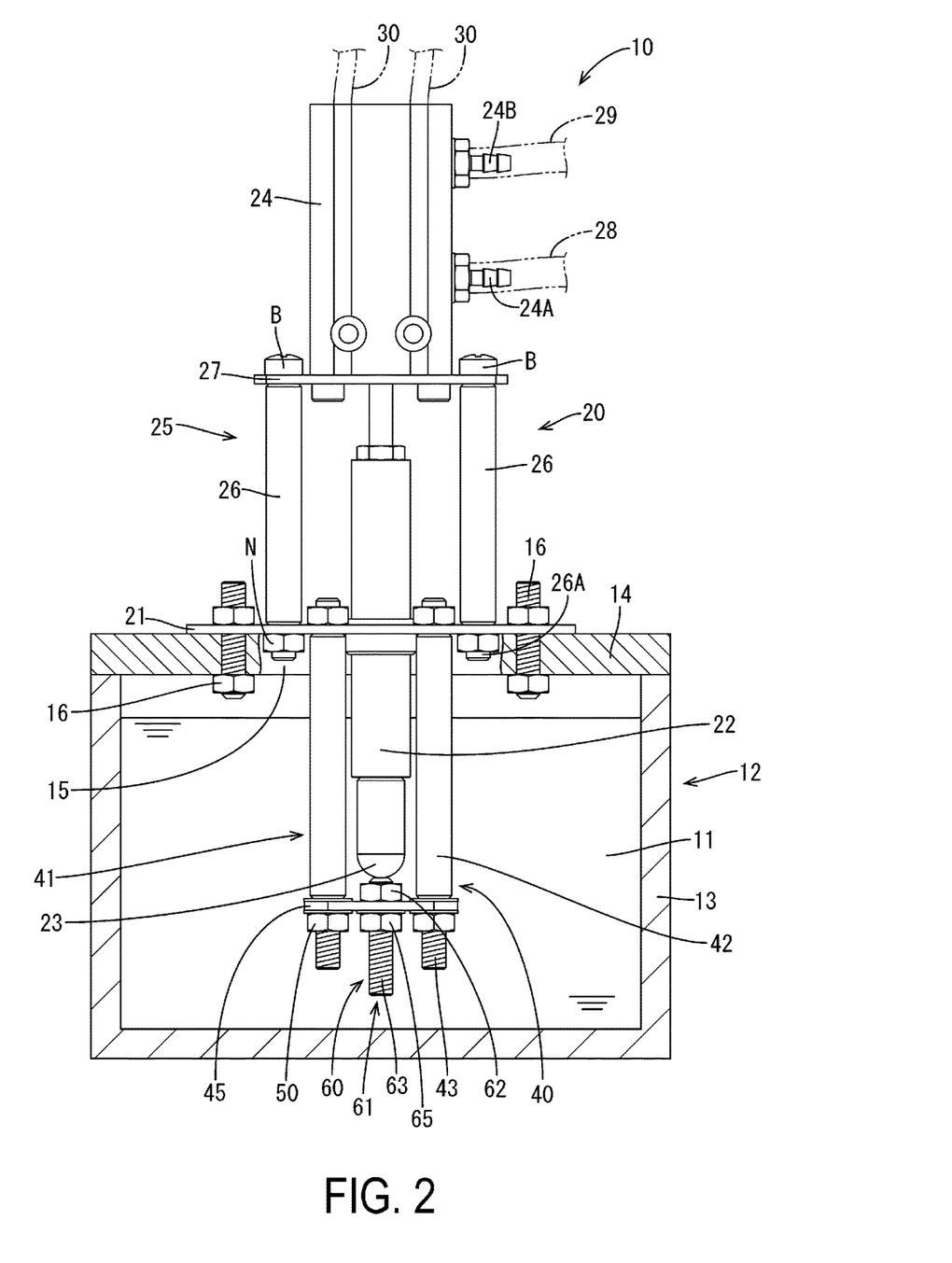
FIG. 2 is a partial cutaway cross-sectional view illustrating a state where a cylinder strikes and presses the head of a center bolt.
Figure 3:
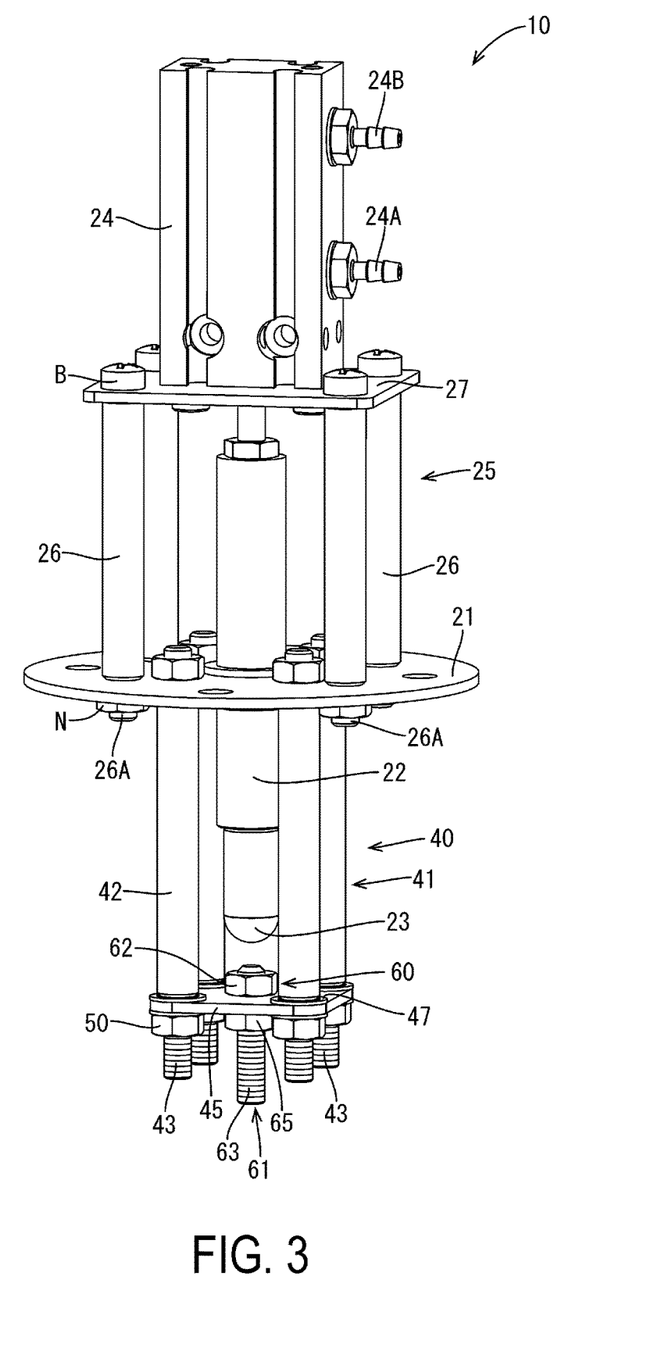
FIG. 3 is a perspective view illustrating a state of a nucleation device as seen from diagonally above.
Figure 4:
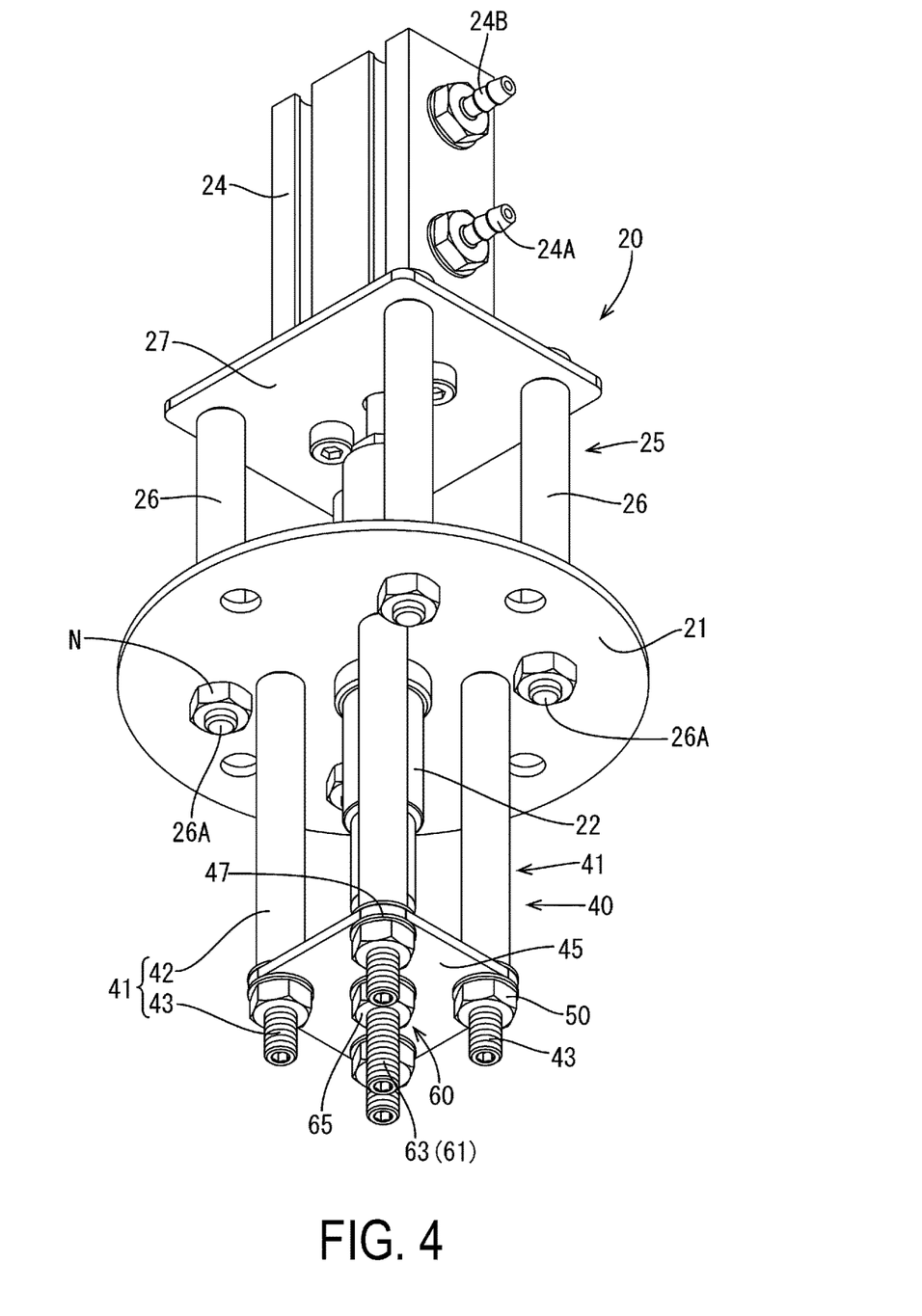
FIG. 4 is a perspective view illustrating a state of the nucleation device as seen from diagonally below.
Figure 5:
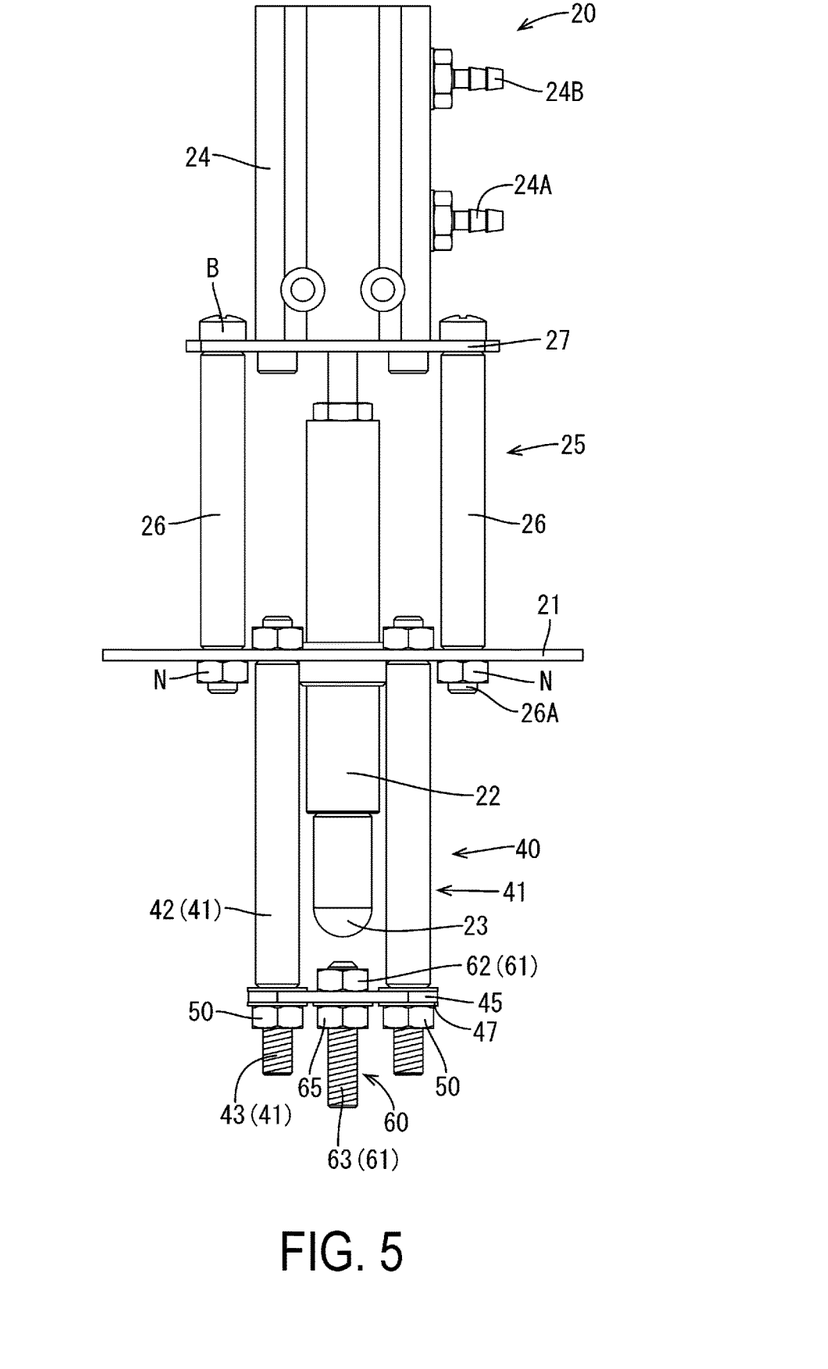
FIG. 5 is a front view of the nucleation device.
Figure 6:
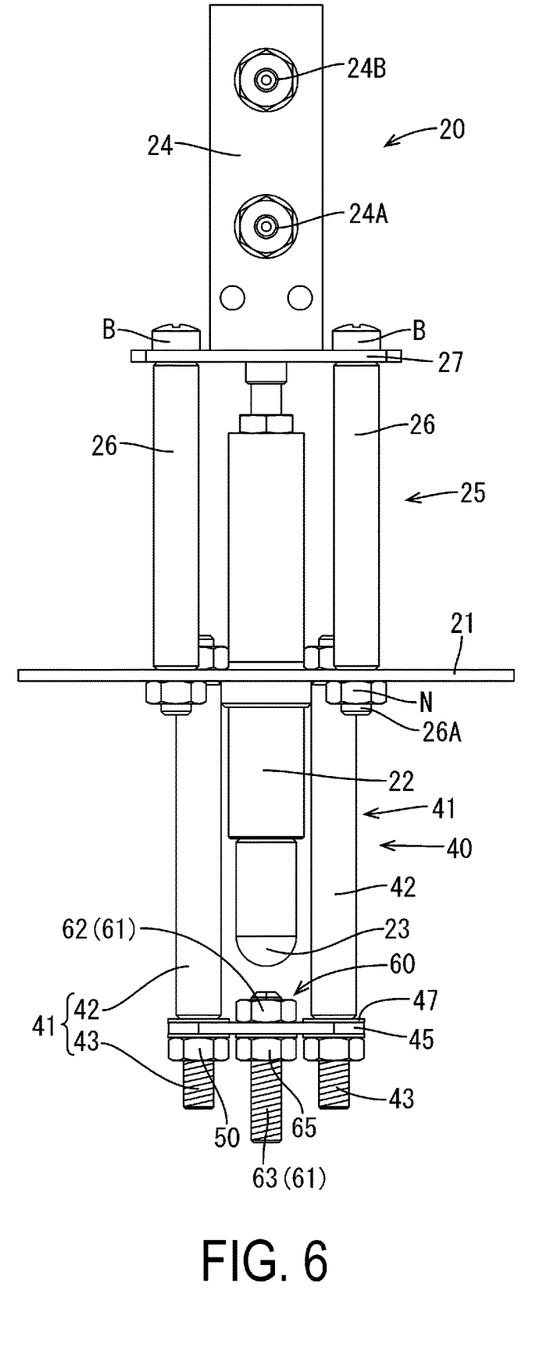
FIG. 6 is a side view of the nucleation device.

As illustrated in FIGS. 1 and 2, the heat storage device 10 has a configuration including the heat storage material 11, a container 12 that houses the heat storage material 11, and a nucleation device 20 attached to the container 12 while disposed within the heat storage material 11.

The heat storage material 11 is formed from sodium acetate trihydrate in a stable supercooled state, and generates heat when phase changing from the supercooled state (from a liquid state to a solid state). Note that any known heat storage material may be used as the heat storage material 11, provided that it phase changes from a supercooled state.

The container 12 is formed from a heat-resistant synthetic resin and, as illustrated in FIGS. 1 and 2, has a configuration including a container body 13 opening upwards, and a lid portion 14 for closing the upper end opening of the container body 13.

The heat storage material 11 and a lower end portion of a trigger unit 40 of the nucleation device 20 (described later), disposed in the heat storage material 11, are housed in the container body 13.

The lid portion 14 is fixed to the container body 13 so as to close the upper end opening of the container body 13. Additionally, attachment holes 15 for attaching the nucleation device 20 are formed in the lid portion 14 so as to penetrate in the up-down direction, and the heat storage material 11 is sealed in the container 12 as a result of the lid portion 14 being fixed to the container body 13 while the nucleation device 20 is attached to the attachment holes 15.

As illustrated in FIGS. 1 to 6, the nucleation device 20 has a configuration including a fixing member 21 that is fixed to the lid portion 14 of the container 12, a trigger unit 40 that is disposed within the container body 13 of the container 12, an air cylinder 22 that presses the trigger unit 40, a drive unit 24 that drives the air cylinder 22, and a pedestal portion 25 that supports the drive unit 24.

Figure 7:
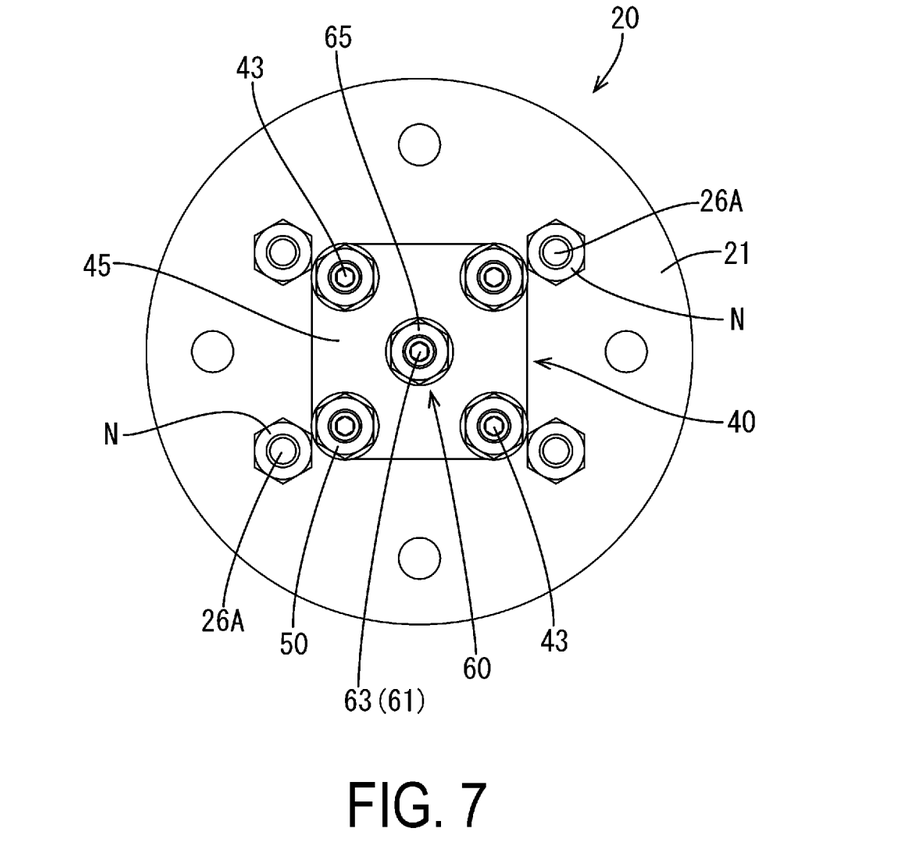
FIG. 7 is a bottom view of the nucleation device.
Figure 8:
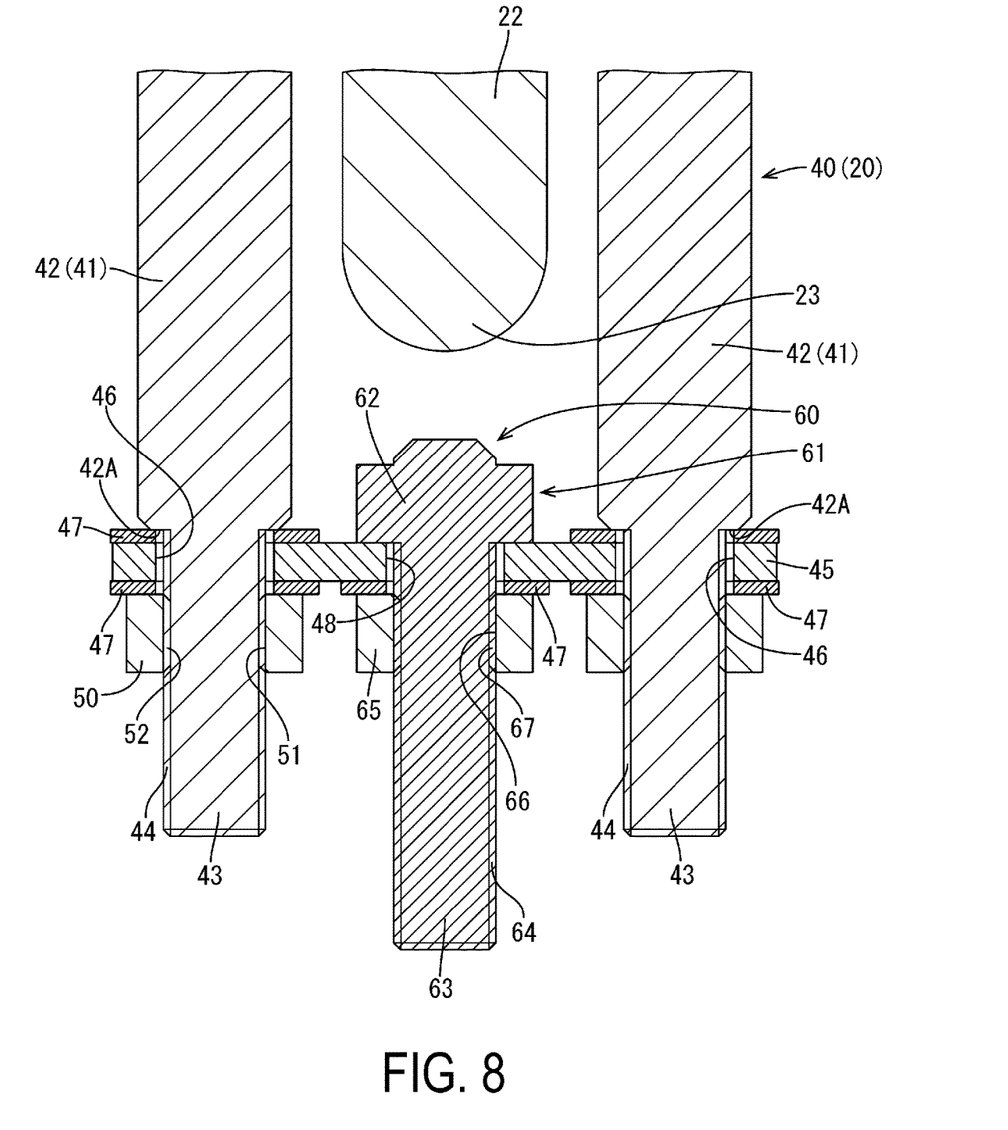
FIG. 8 is an enlarged cross-sectional view of main components of the nucleation device.

The fixing member 21 is made from metal and, as illustrated in FIG. 7, has a substantially round plate-like shape. Additionally, the fixing member 21 is disposed on a top surface of the lid portion 14 so as to protect the attachment holes 15 of the lid portion 14, and the lid portion 14 and the fixing member 21 are fastened together and fixed by a plurality of fastening members 16. Note that a seal is formed between the lid portion 14 and the fixing member 21 by a sealing member (not illustrated).

The pedestal portion 25 is made from metal and has a configuration including four support pillars 26 extending upward from the fixing member 21, and a plate-like pedestal body 27 disposed on upper ends of the four support pillars 26. The four support pillars 26 are disposed so as to surround a center of the fixing member 21. The support pillars 26 are fixed to the fixing member 21 by screw portions 26A provided at lower ends of the support pillars 26 being passed through the fixing member 21 and nuts N being screwed onto the screw portions 26A. The pedestal body 27 has a substantially rectangular shape. The pedestal body 27 is fixed to the four support pillars 26 by inserting bolts B through the four corners of the pedestal body 27 and screwing the bolts B into each of the support pillars 26. Additionally, the drive unit 24 is screwed into a top surface of the pedestal body 27.

The drive unit 24 has a substantially rectangular solid block shape that is long in the up-down direction. A metal air cylinder 22 penetrating the pedestal body 27 and the fixing member 21 in the up-down direction is provided so as to be movable in the up-down direction in the lower end portion of the drive unit 24.

The air cylinder 22 has a substantially cylindrical shape that is long in the up-down direction. A lower end portion of the air cylinder 22 is configured as a pressing part 23 that has a form consisting of a rounded semispherical shape. Moreover, the pressing part 23 is configured to strike and press the trigger unit 40 as a result of the air cylinder 22 moving downward.

Additionally, an input port 24A for inputting air from an air supply line 28 and an output port 24B for discharging air to an air discharge line 29 are provided vertically juxtaposed on a side surface of the drive unit 24; and electrical cables 30, on which a switch (not illustrated) is provided for switching the drive unit 24 ON and OFF, are attached to a top surface of the drive unit 24.

Moreover, in this configuration, by switching the switch from OFF to ON, air from the input port 24A is taken into the drive unit 24, and the air cylinder 22 is moved swiftly in the up-down direction due to the pressure of the air. Note that the force moving the air cylinder 22 can be adjusted by adjusting the pressure of the air supplied from the air supply line 28, and the pressure of the air may be any pressure that is higher than or equal to 0.15 MPa (mega pascals), but is preferably about from 0.15 to 0.6 MPa.

The trigger unit 40 is made from metal and has a configuration including the plurality of holding pillars 41 (one example of the substrate or the fastened portion; four in the present specification) extending downward from the fixing member 21, a trigger plate 45 (one example of the substrate or the plate member) disposed on lower ends of the plurality of holding pillars 41, trigger nuts 50 (one example of the substrate or the fastening portion) that fix the trigger plate 45 to the holding pillars 41, and a strike member 60 (one example of the substrate) that is struck by the air cylinder 22.

The holding pillars 41 are disposed at four locations farther inward in a radial direction of the fixing member 21 than the four support pillars 26 of the fixing member 21. Each of the holding pillars 41 is firmly fixed to the fixing member 21 by tightening the Nuts that penetrate the fixing member 21 in the holding pillars 41 from above. Additionally, each of the holding pillars 41 includes a pillar body 42 and a shaft portion 43 that includes a male screw portion 44 provided with a small diameter on a lower face 42A of the pillar body 42. A boundary between the pillar body 42 and the shaft portion 43 is formed in a step-shape so that the lower face 42A of the pillar body 42 is substantially horizontal.

The trigger plate 45 has a substantially rectangular flat plate shape. Through-holes 46 that penetrate the trigger plate 45 in the up-down direction are provided in each of the four corners of the trigger plate 45. A center through-hole 48 that penetrates the trigger plate 45 in the up-down direction in the same manner as the through-holes 46 is provided in substantially a center portion of the trigger plate 45.

The through-holes 46 of the four corners are configured such that the shaft portion 43 of each of the holding pillars 41 can be inserted therethrough. The trigger plate 45 is fixed to the four holding pillars 41 by screwing and tightening a trigger nut 50 onto each of the shaft portions 43 while the shaft portion 43 of the holding pillar 41 is inserted through the through-hole 46.

Note that, a washer 47 may be mounted between the pillar body 42 of each of the holding pillars 41 and the trigger plate 45 and between the trigger plate 45 and each of the trigger nuts 50 to prevent loosening and the like of the trigger nuts 50. Tightening torque at which the trigger nuts 50 are tightened onto the shaft portion 43 of the holding pillars 41 is preferably about from 0.5 to 1.45 N·m (Newton-meters).

Specifically, the trigger nut 50 has a typical shape including a fastening hole 51 through which the shaft portion 43 of the holding pillar 41 is inserted, and a female screw portion 52 capable of being screwed onto the male screw portion 44 of the shaft portion 43 is provided on an inner peripheral surface of the fastening hole 51.

Accordingly, when the trigger nut 50 is screwed onto the shaft portion 43 of each of the holding pillars 41 while the shaft portions 43 of the holding pillars 41 are inserted through the through-holes 46 of the trigger plate 45, the trigger plate 45 is sandwiched on both sides in the up-down direction by the lower faces 42A of the pillar bodies 42 of the holding pillars 41 and the trigger nuts 50, with the washers 47 interposed therebetween. As a result, a state is achieved where the holding pillars 41, the trigger plate 45, and the trigger nuts 50 are in close contact with each other, with the washers 47 interposed therebetween, and the male screw portion 44 of the shaft portion 43 of each of the holding pillars 41 and the female screw portion 52 of the fastening hole 51 of each of the trigger nuts 50 are in close contact with each other. Thus, the trigger plate 45 is fixed to the lower end portions of the four holding pillars 41.

On the other hand, the strike member 60 is fixed at substantially a center portion of the trigger plate 45, within a movement path of the air cylinder 22. Additionally, the strike member 60 has a configuration including a strike bolt 61 (one example of the fastened portion) and a tightening nut 65 (one example of the fastening portion) capable of tightening the strike bolt 61. The strike bolt 61 is a bolt with a typical shape, and has a form including a head portion 62 and a bolt shaft portion 63 that has a male screw portion 64; and the bolt shaft portion 63 is continuous under the head portion 62. The bolt shaft portion 63 of the strike bolt 61 is insertable through the center through-hole 48 in substantially the center portion of the trigger plate 45. Additionally, the tightening nut 65 has the same form as the trigger nut 50, includes a fastening hole 66 provided with a female screw portion 67, and is capable of being tightened on the bolt shaft portion 63 of the strike bolt 61 that has been inserted through the center through-hole 48.

Accordingly, when the tightening nut 65 is tightened on the bolt shaft portion 63 of the strike bolt 61 while the bolt shaft portion 63 of the strike bolt 61 is inserted through the center through-hole 48, the trigger plate 45 is sandwiched on both sides in the up-down direction by the head portion 62 of the strike bolt 61 and the tightening nut 65. Thus, the head portion 62 of the strike bolt 61 and the trigger plate 45 achieve a state of close contact with each other, and the trigger plate 45 and the tightening nut 65 achieve a state of close contact with the washer 47 interposed therebetween. Additionally, the male screw portion 64 of the bolt shaft portion 63 of the strike bolt 61 and the female screw portion 67 of the fastening hole 66 of the tightening nut 65 achieve a state of close contact. As such, the strike member 60 is fixed at substantially the center portion of the trigger plate 45, within a movement path of the air cylinder 22, and the strike member 60 is configured to be strikable by the pressing part 23 of the air cylinder 22.

The present embodiment has the configuration described above. Next, the operations and effects of the nucleation device 20 in the heat storage device 10 will be described.

As illustrated in FIG. 1, the lower end portion of the trigger unit 40 of the nucleation device 20 is disposed in the heat storage material 11 that is in a liquid state. The heat storage material 11 is placed in a supercooled state by cooling the heat storage material 11 to a temperature at least lower than the solidification temperature thereof.

While the heat storage material 11 is in the supercooled state, the switch of the drive unit 24 is switched from OFF to ON, the air cylinder 22 is moved downward, and the head portion 62 of the strike bolt 61 is struck by the pressing part 23 of the air cylinder 22.

Upon this striking, the head portion 62 of the strike bolt 61 assumes a state of being pressed by the pressing part 23 of the air cylinder 22 and this impact is transferred between the holding pillars 41 of the trigger unit 40 and the trigger plate 45, between the trigger plate 45 and the tightening nut 65, between the male screw portions 44 of the shaft portions 43 of the holding pillars 41 and the female screw portions 52 of the trigger nuts 50, between the head portion 62 of the strike bolt 61 and the trigger plate 45, between the trigger plate 45 and the tightening nut 65, and between the male screw portion 64 of the bolt shaft portion 63 of the strike bolt 61 and the female screw portion 67 of the tightening nut 65. The heat storage material 11, under the state of close contact, nucleates due to any of the states of close contact changing. As a result, the solidification heat of the heat storage material 11 can be reliably released.

In other words, by switching the switch from an OFF state to an ON state from a remote location, thus eliciting a change in the state of close contact of the constituents of the trigger unit 40, the heat storage material 11 can be caused to nucleate. As such, the nucleation reliability of the heat storage material 11 installed at a remote location can be improved.

Moreover, the heat storage material 11 can be repeatedly caused to nucleate and release solidification heat by heating the heat storage material 11, which has solidified due to the nucleation, to a temperature of a melting point or higher thereof, thus returning the heat storage material 11 to a liquid state and, then, re-cooling the heat storage material 11 to the supercooled state.

In cases where initially disposing the trigger unit 40 in the heat storage material 11 and in cases where disassembling and cleaning the trigger unit 40, the heat storage material 11 (the sodium trihydrate) may not penetrate the portions of the trigger unit 40 that are in close contact. In such cases, for example, by charging a powder of crystallized sodium trihydrate, namely seed crystals, into the portions that are in close contact in the trigger unit 40, the heat storage material 11 will be allowed to penetrate under the state of close contact, and the nucleation of the heat storage material 11 can be more easily induced. Note that the sodium acetate trihydrate powder does not need to be charged into all of the portions that are in close contact, and the charging locations can be selected as desired, depending on the locations where nucleation is desired.

Additionally, according to the present embodiment, the strike bolt 61 of the strike member 60 is directly struck and pressed by the pressing part 23 of the air cylinder 22. As such, for example, compared to cases in which a portion where a state of close contact exists in a trigger unit is indirectly pressed or cases where a strike member is pressed by a pressing part without being struck, changes in the portions where states of close contact exist in the trigger unit 40 can be easily elicited with a small pressing force.

Furthermore, according to the present embodiment, while portions where states of close contact exist in the trigger unit 40 are provided throughout a plurality of locations, changes in the states of close contact at a plurality of locations can be simultaneously elicited as a result of only the striking of the strike bolt 61 of the strike member 60 by the air cylinder 22. As such, the nucleation reliability of the heat storage material 11 can be improved.

Additionally, according to the present embodiment, preparation is completed by simply disposing the trigger unit 40 in the heat storage material 11. As such, there is no need to prepare a material that serves as the nucleus of the nucleation (for example, sodium acetate anhydrate or the like), and workability is excellent.

Second Embodiment

Figure 9:
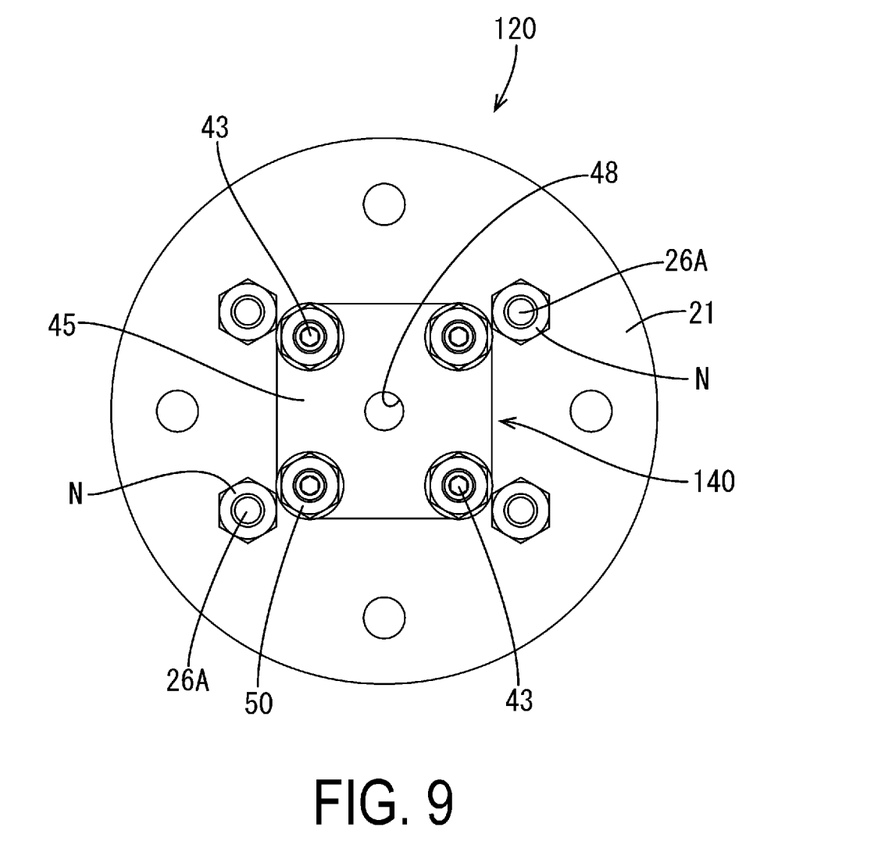
FIG. 9 is a bottom view of a nucleation device according to a second embodiment.
Figure 10:
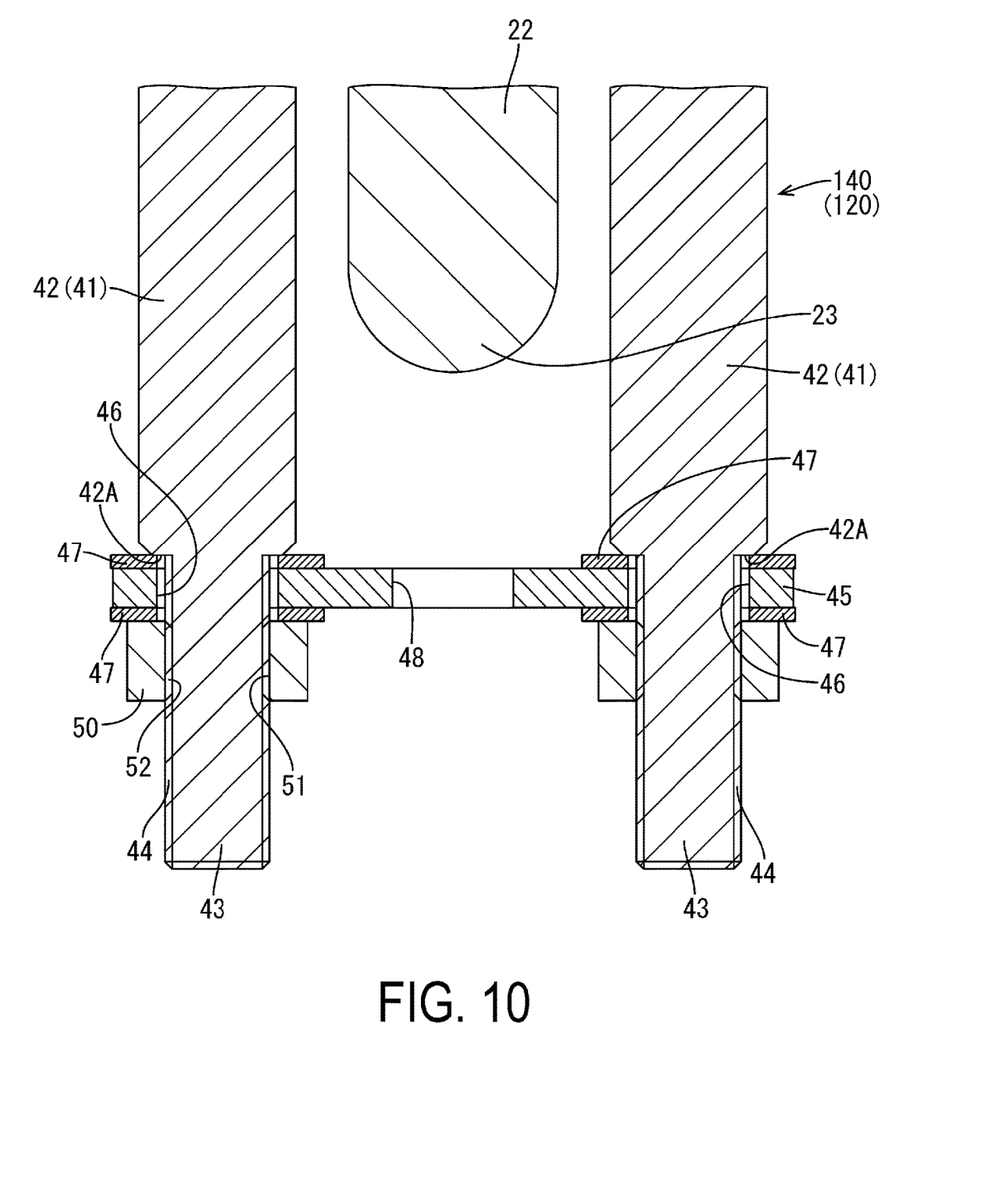
FIG. 10 is an enlarged cross-sectional view of main components of the nucleation device.

Next, a second embodiment is described while referencing FIGS. 9 and 10.

A nucleation device 120 of the second embodiment is realized by modifying the configuration of the trigger unit 40 of the first embodiment. Configurations, operations, and effects common to both the first embodiment and the second embodiment are redundant and, as such, description thereof is omitted. Additionally, the same reference signs are used in the second embodiment to indicate constituents that are the same as those in the first embodiment.

A trigger unit 140 of the second embodiment is the same as that in the first embodiment with the exception that the strike member 60 of the trigger unit 40 is removed. In this configuration, the trigger plate 45 is struck by the pressing part 23 of the air cylinder 22, and a position separated from the portions in close contact in the trigger unit 140 is pressed.

Accordingly, a substantially center portion of the trigger plate 45 is struck by the pressing part 23 of the air cylinder 22, thereby eliciting a change in the state of close contact between the holding pillars 41 and the trigger plate 45, and between the trigger plate 45 and the trigger nuts 50 and also eliciting a change in the state of close contact of the male screw portion 44 of the shaft portion 43 of each of the holding pillars 41 and the female screw portion 52 of each of the trigger nuts 50, thereby causing the nucleation of the heat storage material 11. As a result, the number of components of the trigger unit 40 can be reduced.

Third Embodiment

Figure 11:
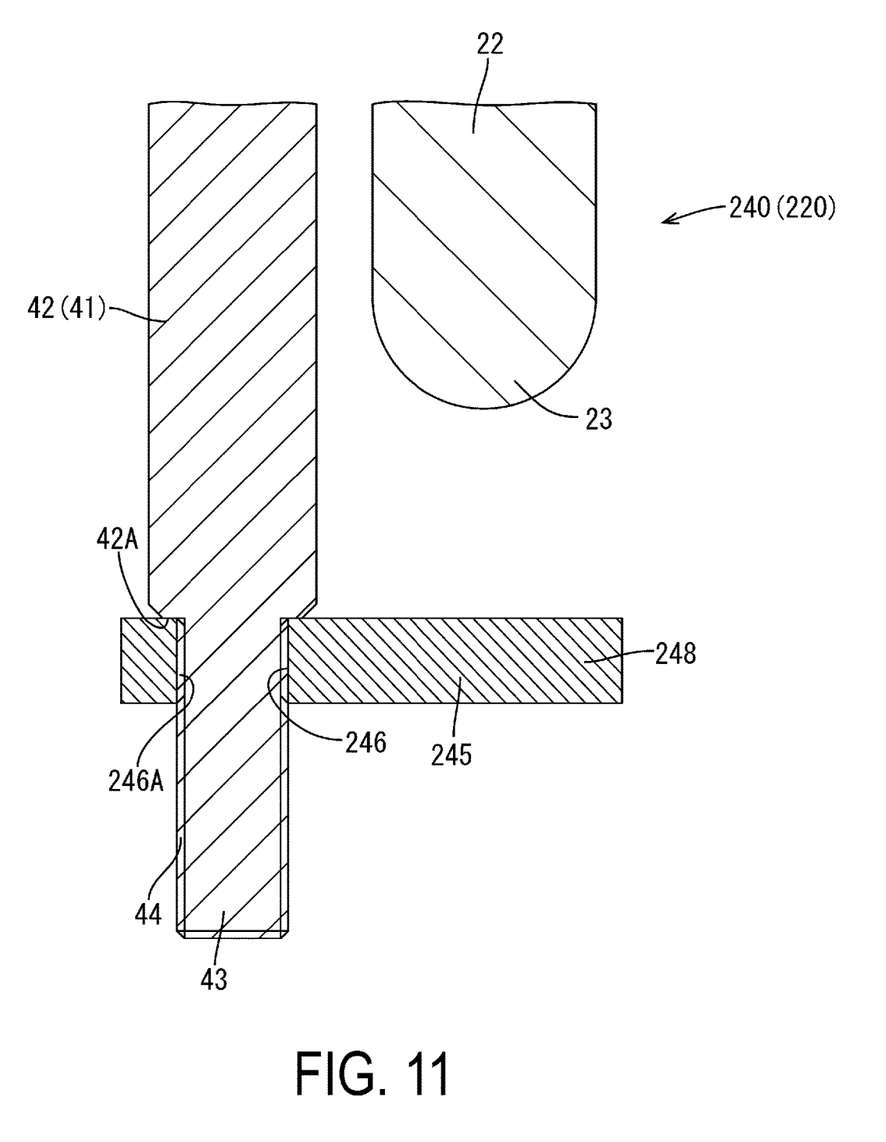
FIG. 11 is an enlarged cross-sectional view of a nucleation device according to a third embodiment.

Next, a third embodiment is described while referencing FIG. 11.

A nucleation device 220 of the third embodiment is realized by modifying the configuration of the trigger unit 40 of the first embodiment. Configurations, operations, and effects common to both the first embodiment and the third embodiment are redundant and, as such, description thereof is omitted. Additionally, the same reference signs are used in the third embodiment to indicate constituents that are the same as those in the first embodiment.

The trigger unit 240 of the third embodiment has a configuration in which one of the holding pillars 41 of the trigger unit 40 of the first embodiment is provided; and a female screw portion 246A, capable of being screwed onto the male screw portion 44 of the shaft portion 43 of the holding pillar 41, is provided on an inner peripheral surface of a through-hole 246 of a trigger plate 245. Note that the female screw portion 246A is formed on the inner peripheral surface of the through-hole 246 and, as such, the plate thickness dimension of the trigger plate 245 is greater than that of the trigger plate 45 of the first embodiment.

That is, trigger plate 245 of the present embodiment, a configuration is provided in which the female screw portion 246A of the through-hole 246 is screwed directly onto the shaft portion 43 of the single holding pillar 41, and, thus, the trigger plate 245 is fixed to the single holding pillar 41 in a cantilevered state. A change in the state of close contact of the holding pillar 41 and the trigger plate 245 is elicited by pressing the free end 248 of the trigger plate 245, which results in the nucleation of the heat storage material 11. In other words, according to the present embodiment, the number of components of the trigger unit 240 can be reduced and miniaturization of the nucleation device 220 is possible.

EXAMPLES

Next, the nucleation devices 20 and 120 of the first and second embodiments were operated, and the phase changing of the heat storage material 11 from a liquid state to a solid state was confirmed. The results of each test are shown below.

Test Example 1

In this test, the heat storage material 11 and the trigger unit 140 (in a state where the heat storage material 11 (the sodium trihydrate) has not penetrated the portions that are in close contact) of the nucleation device 120 that had been disassembled and cleaned were set in the container 12 of the second embodiment, and the heat storage material 11 was placed in a supercooled state. Next, the air cylinder 22 of the nucleation device 120 was pressed out at an air pressure of 0.6 MPa, and the trigger plate 45 was struck by the pressing part 23. In this test, the striking was repeated at least 30 times, but nucleation of the heat storage material 11 could not be confirmed.

Additionally, using the same configuration as described above, but repeating the striking at least 20 times at an air pressure in a range from 0.3 to 0.5 MPa, nucleation of the heat storage material 11 could not be confirmed in three out of three tests.

Test Example 2

In this test, in the same manner as in Test Example 1, the heat storage material 11 and the trigger unit 140 of the nucleation device 120 that had been disassembled and cleaned were set in the container 12 of the second embodiment. Then, the heat storage material 11 was placed in a supercooled state and was forcibly caused to nucleate using, for example, seed crystals or the like. Thereafter, without removing the trigger unit 140 from the heat storage material 11, the heat storage material 11 was heated, dissolved, and returned to a liquid state; and the heat storage material 11 was placed again in a supercooled state. Next, the air cylinder 22 was pressed out at an air pressure of 0.6 MPa, and the trigger plate 45 was struck by the pressing part 23. In this case, nucleation of the heat storage material 11 by one strike could be confirmed. Additionally, in this test, the sites where the heat storage material 11 nucleated were the portions where states of close contact existed between the holding pillars 41 and the trigger plate 45, the trigger plate 45 and the trigger nuts 50, and the shaft portions 43 of the holding pillars 41 and the trigger nuts 50.

Additionally, in the same manner as described above, the striking was performed using an air pressure in a range from 0.3 to 0.5 MPa without removing the trigger unit 140 from the once nucleated heat storage material 11 and, in this case, nucleation by one strike could be confirmed in 19 out of 19 tests.

Note that, in the same manner as described above, the sites where nucleation occurred were the portions where states of close contact existed in the trigger unit 140. However, in one out of 19 tests, the trigger nuts 50 were tightened at 1.45 N·m and, in this case, there were fewer nucleation sites.

Test Example 3

In this test, a powder or liquid sodium trihydrate was charged into the portions where states of close contact exist in the trigger unit 140 of the second embodiment that had been cleaned. Then, the heat storage material 11 and the trigger unit 140 were set in the container 12. Next, the air cylinder 22 was pressed out at an air pressure of 0.5 MPa, and the trigger plate 45 was struck by the pressing part 23. In this case, nucleation of the heat storage material 11 by one strike could be confirmed in three out of three tests.

Additionally, as in Test Example 2, the sites where the heat storage material 11 nucleated were the portions where states of close contact existed between the holding pillars 41 and the trigger plate 45, the trigger plate 45 and the trigger nuts 50, and the shaft portions 43 of the holding pillars 41 and the trigger nuts 50.

Test Example 4

In this test, in the same manner as in Test Example 2, the heat storage material 11 was forcibly caused to nucleate. Thereafter, without removing the trigger unit 140 from the heat storage material 11, the heat storage material 11 was heated, dissolved, and returned to a liquid state; and the heat storage material 11 was placed again in a supercooled state. Then, the trigger plate 45 was pressed at an air pressure of 0.5 MPa, from a state where the pressing part 23 of the air cylinder 22 of the nucleation device 20 was in contact with the trigger plate 45.

In this case, nucleation of the heat storage material 11 by one press could be confirmed.

Additionally, in the same manner as in Test Examples 2 and 3, the sites where the heat storage material 11 nucleated were the portions where states of close contact existed in the trigger unit 140.

Note that in cases where the trigger plate 45 was pressed by an air pressure in a range of 0.15 to 0.3 MPa, nucleation of the heat storage material 11 could not be confirmed.

Test Example 5

In this test, first, the heat storage material 11 and the trigger unit 40 of the nucleation device 20 that had been disassembled and cleaned were set in the container 12 of the first embodiment, and the heat storage material 11 was supercooled. Then, the heat storage material 11 was forcibly caused to nucleate using, for example, seed crystals or the like. Thereafter, without removing the trigger unit 40 from the heat storage material 11, the heat storage material 11 was heated, dissolved, and returned to a liquid state; and the heat storage material 11 was placed again in a supercooled state. Next, the air cylinder 22 was pressed out at an air pressure of 0.5 MPa, and the strike member 60 was struck by the pressing part 23. In this case, nucleation of the heat storage material 11 by one strike could be confirmed.

Additionally, as in Test Examples 2 to 4, the sites where the heat storage material 11 nucleated were the portions where states of close contact existed in the trigger unit 140.

Conclusion

As described above, nucleation of the heat storage material 11 could not be confirmed in Test Example 1 in which the trigger unit 140 was disassembled and cleaned and, thereafter, the heat storage material 11 did not penetrate into the portions where the state of close contact existed in the trigger unit 140 (between the holding pillars 41 and the trigger plate 45, the trigger plate 45 and the trigger nuts 50, and the shaft portion 43 of the holding pillars 41 and the trigger nuts 50). In contrast, nucleation of the heat storage material 11 could be confirmed in Test Examples 2 to 5 in which the trigger unit 140 was disassembled and cleaned and, thereafter, it is thought that the heat storage material 11 penetrated into the portions where the state of close contact existed in the trigger unit 140.

That is, it is thought that when the trigger unit 40 is pressed while the heat storage material 11 has penetrated into the portions where the state of close contact exists in the trigger units 40 and 140, each of the states of close contact changes and the heat storage material 11 nucleates due to the material serving as the nucleus under the state of close contact.

OTHER EMBODIMENTS

The technology disclosed in the present specification is not limited by the preceding recitations and/or the embodiments described using the drawings, and various aspects such as the following should be construed to be included.

(1) In the embodiments described above, a configuration was given in which the pressing part 23 of the air cylinder 22 struck and pressed the strike member 60 or the trigger plate 45 or 245. However, the technology disclosed in the present specification is not limited thereto, and a configuration is possible in which pressing is performed in a state where the pressing part is in contact with the strike member or the trigger plate.

(2) In the embodiments described above, a configuration was given in which the washer 47 was provided between the holding pillars 41 and the trigger plate 45 or 245, between the trigger plate 45 or 245 and the trigger nuts 50, and between the trigger plate 45 and the tightening nut 65. However, the technology disclosed in the present specification is not limited thereto, and a configuration is possible in which, for example, the frequency at which the trigger nuts are re-tightened is increased and the washers are not provided.

(3) In the embodiments described above, a configuration was given in which the container 12 is formed from a synthetic resin. However, the technology disclosed in the present specification is not limited thereto, and a configuration is possible in which the container is formed from a metal such as stainless steel (SUS), aluminum, or the like.

(4) In the embodiments described above, a configuration was given in which the drive unit 24 used air pressure to move the air cylinder 22 up and down. However, the technology disclosed in the present specification is not limited thereto, and a configuration is possible in which an actuator such as a motor or solenoid is used.

REFERENCE SIGNS LIST

10 Heat storage device
11 Heat storage material
12 Container
20, 120, 220 Nucleation device
23 Pressing part
41 Holding pillar (one example of the substrate or fastened portion)
44 Male screw portion of the holding pillar
45, 245 Trigger plate (one example of the substrate or plate member)
50 Trigger nut (one example of the substrate or fastening portion)
53 Female screw portion of the trigger nut
60 Strike member (one example of the substrate)
61 Strike bolt (one example of the fastened portion)
65 Tightening nut (one example of the fastening portion)
67 Female screw portion of the tightening nut

The invention claimed is:

1. A heat storage device, comprising:
a heat storage material that phase changes from a liquid to a solid state;
a nucleation device located in the heat storage material; and
a container that houses the heat storage material and the nucleation device;
wherein the nucleation device comprises a plurality of substrates and a pressing part;
wherein the plurality of substrates comprises a flat plate member, a fastened portion that includes a male screw portion, and a fastening portion that includes a female screw portion;
wherein the fastening portion is screwed onto the fastened portion so as to fix the fastened portion to the flat plate member; and
wherein the nucleation device is configured to move the pressing part such that the pressing part directly impacts the fastened portion in the heat storage material, thereby causing the heat storage material to transition from the liquid state to the solid state.

2. The heat storage device according to claim 1, wherein: the heat storage material is sodium acetate trihydrate.

3. A nucleation method for a heat storage device according to claim 1, the method comprising:
impacting the fastened portion with the pressing part, thereby causing the heat storage material to transition from the liquid state to the solid state.

* * * * *